US011534607B2

United States Patent
Stem et al.

(10) Patent No.: US 11,534,607 B2
(45) Date of Patent: Dec. 27, 2022

(54) METHODS OF SHIELDING IMPLANTABLE MEDICAL LEADS AND IMPLANTABLE MEDICAL LEAD EXTENSIONS

(71) Applicant: MEDTRONIC, INC., Minneapolis, MN (US)

(72) Inventors: Bryan D. Stem, Minneapolis, MN (US); James M. Olsen, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 916 days.

(21) Appl. No.: 16/392,431

(22) Filed: Apr. 23, 2019

(65) Prior Publication Data

US 2019/0247648 A1 Aug. 15, 2019

Related U.S. Application Data

(62) Division of application No. 14/804,020, filed on Jul. 20, 2015, now Pat. No. 10,279,171.

(60) Provisional application No. 62/028,120, filed on Jul. 23, 2014.

(51) Int. Cl.
*A61N 1/05* (2006.01)
*A61N 1/08* (2006.01)
*H01R 43/20* (2006.01)

(52) U.S. Cl.
CPC ............... *A61N 1/08* (2013.01); *A61N 1/05* (2013.01); *H01R 43/20* (2013.01); *A61N 1/086* (2017.08)

(58) Field of Classification Search
CPC . A61N 1/08; A61N 1/05; A61N 1/086; H01R 43/20; H01R 35/02; H01R 33/00; H01R 13/005; H01R 13/58
See application file for complete search history.

(56) References Cited

U.S. PATENT DOCUMENTS

| | | | | |
|---|---|---|---|---|
| 2005/0222658 A1* | 10/2005 | Hoegh | ............... | A61N 1/0553 607/116 |
| 2011/0118815 A1* | 5/2011 | Kuzma | ............... | A61N 1/05 607/116 |
| 2011/0218602 A1* | 9/2011 | Kampa | ............... | A61N 1/05 29/877 |
| 2015/0170792 A1* | 6/2015 | Alford | ............... | A61N 1/05 174/102 R |

\* cited by examiner

*Primary Examiner* — Carl H Layno
*Assistant Examiner* — Anh-Khoa N Dinh
(74) *Attorney, Agent, or Firm* — Withers & Keys, LLC (57) ABSTRACT

A shield layer is added to an existing lead or lead extension by applying the shield layer to the lead body between the proximal contact and distal electrode of the lead body. The shield layer may be covered with an outer insulative layer. An inner insulative layer may be applied over the lead body prior to adding the shield layer and the outer insulative layer. The shield layer may have a terminator applied to the end of the shield layer to prevent migration of the shield layer through the outer insulative layer. The shield layer may be of various forms including a tubular braided wire structure or a tubular foil. The tubular braided wire structure may be applied to the lead body by utilizing the lead body as a mandrel within a braiding machine.

8 Claims, 9 Drawing Sheets

METHODS OF SHIELDING IMPLANTABLE MEDICAL LEADS AND IMPLANTABLE MEDICAL LEAD EXTENSIONS

RELATED APPLICATIONS

The present application is a divisional of U.S. application Ser. No. 14/804,020, now U.S. Pat. No. 10,279,171, filed on Jul. 20, 2015, which claims priority to U.S. Prov. Appl. No. 62/028,120, filed on Jul. 23, 2014.

TECHNICAL FIELD

Embodiments relate to implantable medical leads and implantable medical lead extensions. More particularly, embodiments relate to methods of shielding implantable medical leads and implantable medical lead extensions.

BACKGROUND

Implantable medical systems are used to provide stimulation therapy and/or physiological sensing for patients. The implantable medical system includes a stimulation or sensing device that is implanted at a convenient location. Implantable medical leads are routed between the site of implantation of the device and a target site where stimulation or sensing is to occur. Where the route is lengthy, an implantable medical lead extension is used to traverse a portion of that distance.

The implantable medical leads include one or more electrical contacts located near a proximal end of the lead. Where no extension is needed, the proximal end of the lead is physically connected to the stimulation or sensing device so that the proximal contacts of the lead are electrically coupled to electrical circuitry of the device. For scenarios where the implantable medical lead extension is used, then the proximal end of the lead is physically connected to a distal end of the extension where electrical connectors of the extension are coupled to the electrical contacts of the lead. The proximal end of the extension is physically connected to the stimulation or sensing device so that the proximal contacts of the extension are electrically coupled to electrical circuitry of the device. The leads also include one or more electrodes located near a distal end of the leads. Electrical conductors are present within the lead, and each electrical conductor is connected to a respective electrical contact and electrode to provide an electrical path for stimulation and/or sensed signals. Electrical conductors are also present within the extension, and each electrical conductor is connected to a respective electrical contact and distal connector to provide an electrical path for stimulation and/or sensed signals.

Because the lead and lead-extension combination extends over a significant distance within the body, each electrical conductor within the lead and extension is susceptible to receiving extraneous electromagnetic energy that produces electrical current on the electrical conductor. While most ambient conditions expose the lead and lead extension to insignificant levels of such extraneous electromagnetic energy, certain situations may create levels of extraneous electromagnetic energy that are of concern. An example of such a situation is a magnetic resonance imaging (MRI) scan. The MRI scan utilizes a high energy radio frequency (RF) electromagnetic signal. This RF signal may produce relatively large levels of electrical current on the electrical conductor of the lead and extension when the patient having the implantable medical system that includes the lead and/or lead extension combination undergoes the MRI scan. The relatively large electrical current that results from the high energy RF signal produces heating at the electrodes that may create discomfort and even dangerous tissue damage at the site within the body where the one or more electrodes of the lead are located.

It has been found that a shield layer within the lead reduces the amount of RF energy that reaches the electrical conductors, which in turn reduces the amount of current being coupled onto the electrical conductors and reduces the heating at the electrodes to acceptable levels. The manufacturing process of the lead has been altered to include a shield layer when the lead body is being manufactured by creating an inner jacket over the electrical conductor, then creating the shield layer on the inner jacket, and then creating an outer jacket over the inner jacket. The electrical contacts and electrodes are then installed about the inner jacket and are coupled to the electrical conductor to complete the leads. However, leads and extensions that have been constructed without such shield layers or other protective aspects remain vulnerable to the high levels of RF energy of the MRI scan or other situation.

SUMMARY

Embodiments address issues such as these and others by adding a shield layer onto the exterior surface of an insulative lead body of an existing lead having electrical contacts and electrodes already installed on that lead body. The shield layer is then covered by an insulative layer.

Embodiments provide a method of shielding an implantable medical lead. The method involves providing a shield layer onto an exterior surface of an insulative lead body of the implantable medical lead between an electrical contact on a proximal end of the insulative lead body and an electrode on a distal end of the insulative lead body with a proximal end of the shield layer being spaced distally from the electrical contact and with a distal end of the shield layer being spaced proximally from the electrode. The method further involves applying an outer insulative layer onto the shield layer while the shield layer is present on the exterior surface of the insulative layer with the outer insulative layer being located between the electrical contact and the electrode.

Embodiments provide a method of shielding an implantable medical lead. The method involves utilizing the implantable medical lead as a mandrel for a braiding machine to braid wires onto an insulative lead body of the implantable medical lead between an electrical contact on a proximal end of the implantable medical lead and an electrode on a distal end of the implantable medical lead with a proximal end of the shield layer being spaced distally from the electrical contact and with a distal end of the shield layer being spaced proximally from the electrode. The method further involves applying an outer insulative layer onto the braided wires while the braided wires are present on the insulative lead body of the implantable medical lead with the outer insulative layer being located between the electrical contact and the electrode.

Embodiments provide a method of shielding an implantable medical lead extension. The method involves providing a shield layer onto an exterior surface of an insulative lead body of the implantable medical lead extension between an electrical contact on a proximal end of the implantable medical lead extension and a distal end of the implantable medical lead extension with a proximal end of the shield layer being spaced distally from the electrical contact. The method further involves applying an outer insulative layer onto the shield layer with the outer insulative layer being located between the electrical contact and the distal end.

Embodiments provide a method of shielding an implantable medical lead extension. The method involves utilizing the implantable medical lead extension as a mandrel for a braiding machine to braid wires onto an insulative lead body of the implantable medical lead extension between an electrical contact on a proximal end of the implantable medical lead extension and a distal end of the implantable medical lead extension with a proximal end of the shield layer being spaced distally from the electrical contact. The method further involves applying an outer insulative layer onto the braided wires on the implantable medical lead extension with the outer insulative layer being located between the electrical contact and the distal end.

Embodiments provide an implantable medical lead that includes a lead body defining a lumen, a conductor within the lumen, a proximal contact coupled to a proximal area of the lead body, and a distal electrode coupled to a distal area of the lead body, with the conductor electrically coupling the proximal contact to the distal electrode. The implantable medical lead further includes an inner insulative layer coupled to the outer surface of the lead body, a shield layer positioned about the inner insulative layer and between the proximal contact and the distal electrode, and an outer insulative layer positioned about the shield layer and between the proximal contact and the distal electrode.

Embodiments provide an implantable medical lead extension that includes a lead body defining a lumen, a conductor within the lumen, a proximal contact coupled to a proximal area of the lead body, and a distal connector housing coupled to a distal area of the lead body with a distal connector positioned within the distal connector housing, the conductor electrically coupling the proximal contact to the distal connector. The implantable medical lead extension further includes an inner insulative layer coupled to the outer surface of the lead body, a shield layer positioned about the inner insulative layer and between the proximal contact and the distal connector housing, and an outer insulative layer positioned about the shield layer and between the proximal contact and the distal connector housing.

DETAILED DESCRIPTION

Embodiments provide a shield layer for an existing implantable lead and/or implantable lead extension. This provides a method of manufacturing a lead or extension with a shield layer where a conventional manufacturing technique may be used to create a complete lead or lead extension and then the shield layer is added as a subsequent process. This further provides the ability to retrofit the shield layer to leads and lead extensions that have already been constructed and are present in available inventory so that this existing inventory is made safer for MRI scans.

Figure 1:
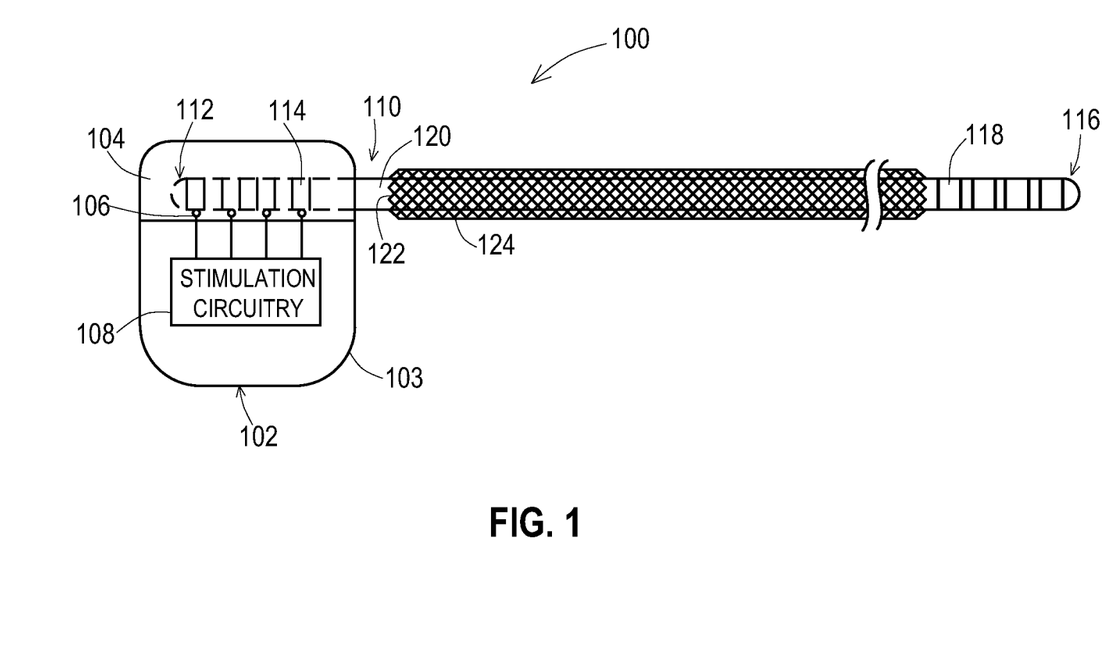
FIG. 1 shows an example of an implantable medical system that includes a lead having an added shield layer according to various embodiments.

FIG. 1 shows one example of an implantable medical system 100 that includes an implantable medical device 102 coupled to an implantable medical lead 110. A proximal end 112 of the lead 110 is present within a connection block 104 of the medical device 102 where electrical contacts 114 of the lead 110 are electrically connected to connectors 106 of the connection block 104. The connectors 106 are electrically coupled to stimulation and/or sensing circuitry 108 within a housing 103 of the medical device 102. A distal end 116 of the lead is routed to the stimulation site where electrodes 118 on the distal end 116 provide the stimulation signals to the tissue and/or sense signals from the tissue. Electrical conductors are present inside the lead 110 to electrically connect the contacts 114 with the electrodes 118.

According to the embodiment shown, the lead 110 has an added shield layer 122 that has been applied to an existing outer layer 120 of the lead body of the lead 110. This shield layer 122 may be of various forms such as a tubular structure of braided conductive wires that have been overbraided atop the existing outer insulative layer 120, a tubular conductive foil structure, and the like. For a braided shield, the wires of the braid may be a conductor such as a biocompatible metal like tantalum, titanium, and the like. For a foil shield, the foil may be a conductor such as biocompatible metal like tantalum, titanium, and the like.

Where the shield layer 122 is a braided wire shield as shown in FIG. 1, the braid may be created with a variety of shield parameters. Examples of shield parameters such as braid angle, wire cross-sectional shape and diameter, number of braid wires, braid depth, distance from shield termination to closest contact or electrode, and the like that may also be used for the embodiments being disclosed herein are described in U.S. patent application Ser. No. 13/264,067, which is incorporated herein by reference in its entirety.

As can be seen, the added shield layer 122 is present with a proximal end of the shield layer 122 starting distally of a most distal proximal contact 114 and ending proximally of a most proximal distal electrode 118. Likewise, an outer insulative layer 124 is applied atop the shield layer 122 with a proximal end of the outer insulative layer 124 starting distally of the most distal proximal contact 114 and ending proximally of the most proximal distal electrode 118 to thereby entirely cover the added shield layer 122. This prevents exposure of the added shield layer 122 to the tissue surround the lead 110.

While the shield layer 122 is not in direct contact with the tissue along the length of the lead 110, high frequency RF energy coupled onto the shield layer 122, such as during an MRI scan, may capacitively couple to the surrounding tissue to dissipate the RF energy over the length of the shield layer 122. Thus, there is a significant amount of tissue where the RF energy is being dissipated, rather than a small amount of tissue where the electrodes 118 are located. Furthermore, if desired, ground rings could be added atop the shield layer 122 where the ground rings are exposed to provide a direct path for current from the shield layer 122 to the tissue or from the shield layer 122 to a ground connection at the device 102.

Thus, the lead 110 may be manufactured in a conventional manner and then the shield layer 122 and insulative layer 124 may be added as subsequent steps. Furthermore, the lead 110 may exist in inventory and may be retrieved from inventory for a retrofit of the shield layer 122 and insulative layer 124.

Figure 2:
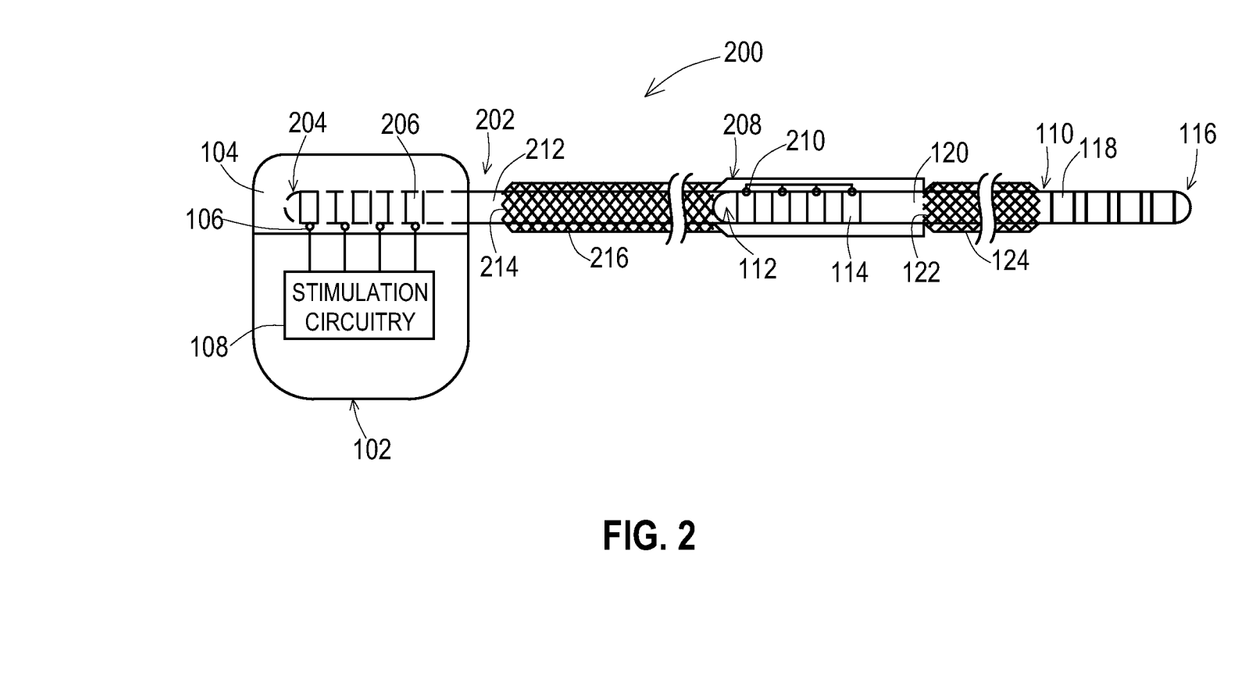
FIG. 2 shows an example of an implantable medical system that includes a lead extension having an added shield layer according to various embodiments.

FIG. 2 shows one example of an implantable medical system 200 that includes the implantable medical device 102 coupled to an implantable medical lead extension 202 that is in turn coupled to the implantable medical lead 110. A proximal end 112 of the lead 110 is present within a distal connection block 208 of the extension 202 where electrical contacts 114 of the lead 110 are electrically connected to connectors 210 of the connection block 208 of the extension. A proximal end 204 of the extension 202 is coupled to the connection block 104 of the medical device 102 where electrical contacts 206 of the extension are electrically connected to connectors 106 of the connection block 104. The distal end 116 of the lead is routed to the stimulation site where the electrodes 118 on the distal end 116 provide the stimulation signals to the tissue and/or sense signals from the tissue. Electrical conductors are present inside the lead 110 to electrically connect the contacts 114 with the electrodes 118 and electrical conductors are present inside the extension 202 to electrically connect the connectors 210 to the contacts 206.

According to the embodiment shown, the extension 202 has an added shield layer 214 that has been applied to an existing outer layer 212 of the lead body of the extension 202. As with the shield layer 122 of the lead 110 in FIG. 1, this shield layer 214 of the extension 202 may be of various forms such as a tubular structure of braided conductive wires that have been overbraided atop the existing outer insulative layer 120, a tubular conductive foil structure, and the like. Where the shield layer 214 is a braided wire shield as shown in FIG. 2, the braid may be created with a variety of shield parameters as described above for the shield layer 122 and as described in U.S. patent application Ser. No. 13/264,067.

As can be seen, the added shield layer 202 is present with a proximal end of the shield layer 214 starting distally of a most distal proximal contact 206 and ending proximally of a most proximal distal connector 210 within the connector block 208. Likewise, an outer insulative layer 216 is applied atop the shield layer 214 with a proximal end of the outer insulative layer 216 starting distally of the most distal proximal contact 206 and ending proximally of the most proximal distal connector 210 to thereby entirely cover the added shield layer 214. This prevents exposure of the added shield layer 214 to the tissue surrounding the extension 202.

While the shield layer 214 is not in direct contact with the tissue along the length of the extension 202, high frequency RF energy coupled onto the shield layer 214, such as during an MRI scan, may capacitively couple to the surrounding tissue to dissipate the RF energy over the length of the shield layer 214. Thus, there is a significant amount of tissue where the RF energy is being dissipated for the extension, rather than a small amount of tissue where the electrodes 118 of the lead 110 are located. Furthermore, if desired, ground rings could be added atop the shield layer 214 where the ground rings are exposed to provide a direct path for current from the shield layer 214 to the tissue or from the shield layer 214 to a ground connection at the device 102.

Thus, the extension 202 may also be manufactured in a conventional manner and then the shield layer 214 and insulative layer 216 may be added as subsequent steps. Furthermore, the extension 202 may exist in inventory and may be retrieved from inventory for a retrofit of the shield layer 214 and insulative layer 216.

As shown in FIG. 2, the lead 110 attached to the extension 202 also includes the added shield layer 122. However, the extension 202 having the shield layer 214 may be used in conjunction with other leads such as leads that have integral shields or even leads that have no shield where the risk of RF coupling to the lead is not as problematic. Similarly, the lead 110 having the added shield layer 122 may be used in conjunction with other extensions including extensions that have integral shields rather than shields that have been added.

Figure 3:
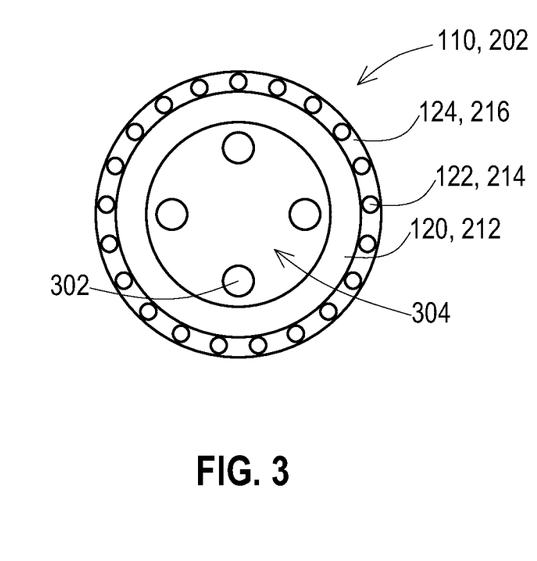
FIG. 3 shows a lateral cross-sectional view of a lead or lead extension having an added shield layer according to various embodiments.

FIG. 3 shows a cross-section of a lead 110 or lead extension 202. The original construction of the lead 110 or lead extension 202 includes the lead body 120, 212. Electrical conductors 302 are present within the lead body 120, 212. The lead body 120, 221 may define a lumen 304 that the conductors 302 pass through when extending from the proximal end to the distal end. The electrical conductors 302 are electrically coupled to the proximal contacts and the distal electrode of the lead or distal connector of the lead extension.

The shield layer 122, 214 is then added about the lead body 120, 212. The shield layer 122, 214 may be added by sliding a loose fitting shield layer, such as the tubular braid of wires or a tubular foil on the lead body 120, 212. Alternatively, the shield layer may be extruded or braided directly onto the lead body 120, 212. This alternative is discussed in more detail below with reference to FIG. 5.

The outer insulative layer 124, 216 is then added over the shield layer 122, 214. The outer insulative layer 124 may be extruded onto the shield layer 122, 214 or may be a tubular structure such as a polyurethane heat shrink tube that fits loosely over the shield layer 122, 214. Once heated the heat shrink tube then shrinks to tightly fit against the shield layer 122, 214 and the lead body 120, 212 which fixes the position of the shield layer 122, 214 and also provides separation of the shield layer 122, 214 from the exterior conditions.

Figure 4:
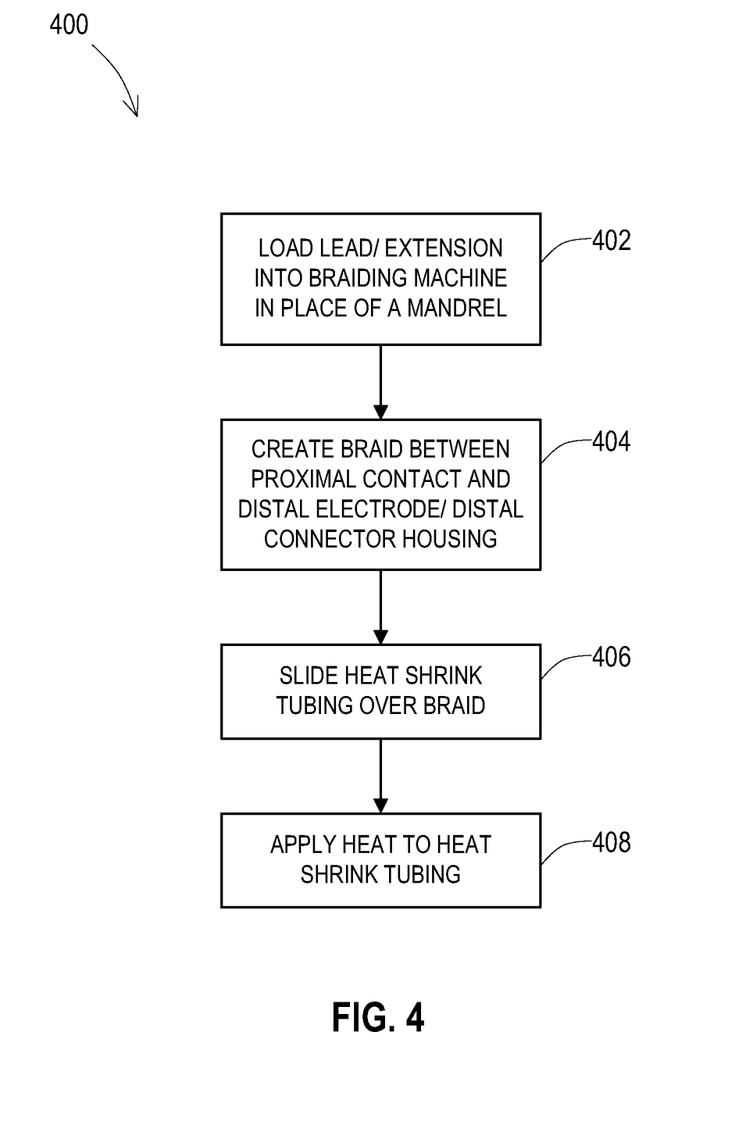
FIG. 4 shows an example of a logical flow of operations to add the shield layer to an existing lead or extension.

One example of operations 400 for constructing the lead or lead extension with the added shield layer is shown in FIG. 4. In this example, the shield layer is a braided tubular structure that is created by braiding the wires directly onto the lead body. At an operation 402, the lead body of the lead or lead extension is loaded into a braiding machine that ordinarily braids wires onto a mandrel. However, the lead body acts as the mandrel. The braid is then created onto the lead body between the proximal contact and the distal electrode or distal connector housing at an operation 404. In this example, a heat shrink tubing is used to provide the outer insulative layer. This heat shrink tubing is positioned by sliding the tubing over the braided shield layer now present on the lead body at an operation 406. Heat is then applied to the heat shrink tubing to cause it to shrink against the braided shield layer at an operation 408.

Figure 5:
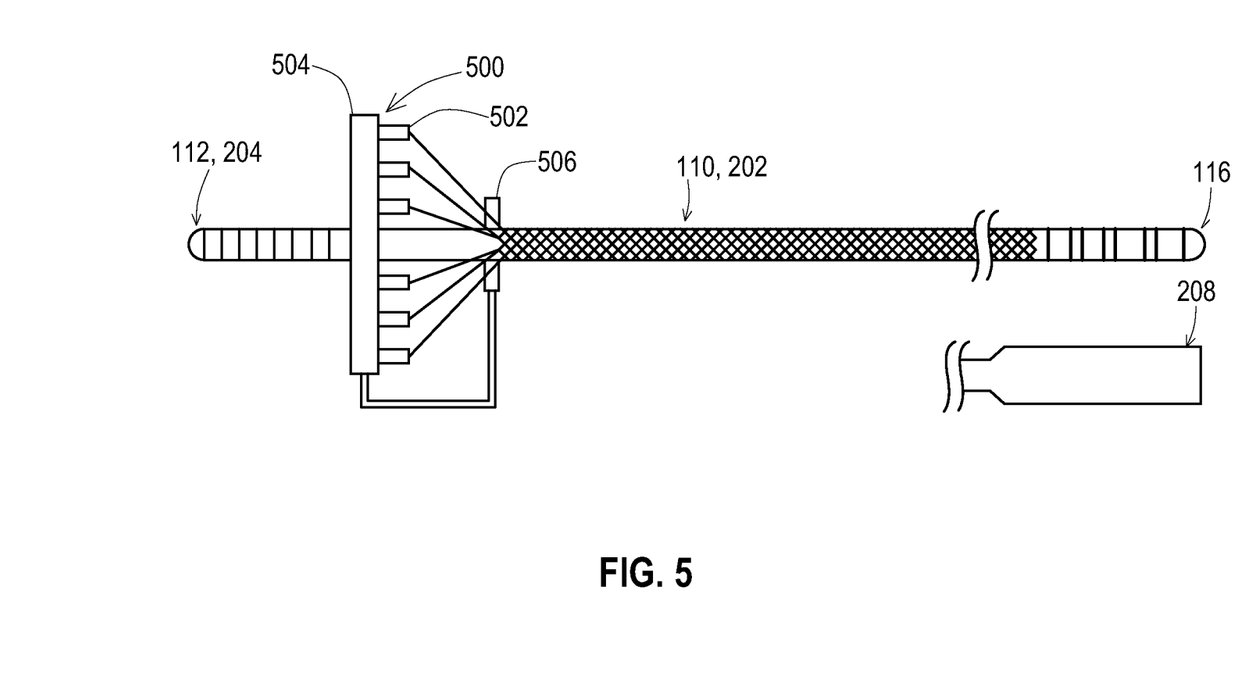
FIG. 5 shows an example of a braiding machine configuration for adding a braided shield layer to an existing lead.

An example of the braiding machine configuration that may be used to complete the operations 402 and 404 of FIG. 4 is shown in FIG. 5. The conventional braiding machine 500 includes a spool support 504, individual spools of wire 502, and a braiding mechanism 506 that guides the wires into the braided configuration onto a mandrel. However, in this configuration, the lead 110 or lead extension 202 is fed through the braiding mechanism 506 in place of a mandrel. As the lead 110 or lead extension 202 moves to the right as shown, the wires are braided onto the lead body.

Figure 6:
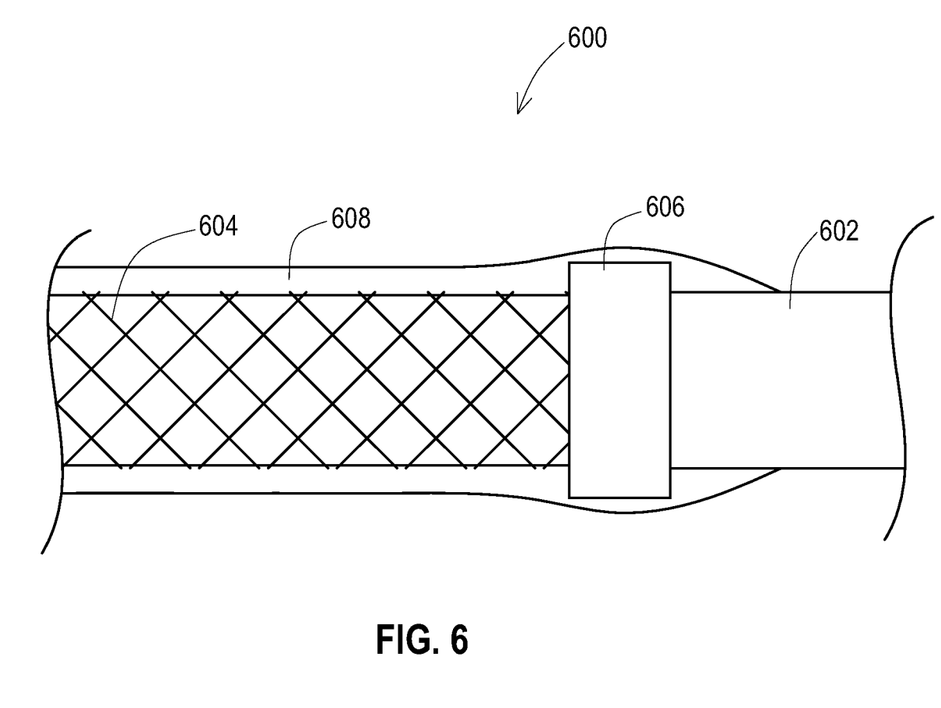
FIG. 6 shows an example of a lead or lead extension having an added shield layer with a shield terminator.

FIG. 6 shows another embodiment of a lead or lead extension 600 that has a shield layer 604 that has been added to the lead body 602. Prior to application of the outer insulative layer 608, a shield terminator 606 is positioned over the end of the shield layer 604. The shield terminator 606 may be of various forms. For instance, the shield terminator 606 may be a ring that is crimped onto the end of the shield layer 604. This is particularly beneficial for a braided wire shield layer as the ring terminator 606 contains the braid wires and prevents the braid wires from migrating radially through the insulative layer 608. As another example, the terminator 606 may be a polyurethane heat shrink terminator that covers only the end portion of the shield layer 604 and is heated to contain the end of the shield layer 604.

As shown, the insulative layer 608 is applied over the shield layer 604 and may also be applied over the shield terminator 606. Where the terminator 606 is a heat shrink terminator, the result is a heat shrink terminator then covered by an outer insulative layer 608 that may also be a heat shrink tubing.

Alternatively, where the terminator is a biocompatible conductive material such as a biocompatible metal ring, the insulative layer 608 may be stopped prior to covering the shield terminator 606 which allows the shield terminator 606 be exposed to the external conditions. This allows the terminator 606 to provide a ground path from the shield layer to a ground connector of the implantable device 102 that electrically couples to the terminator 606 or a ground path directly to tissue in contact with the terminator 606.

Figure 7:
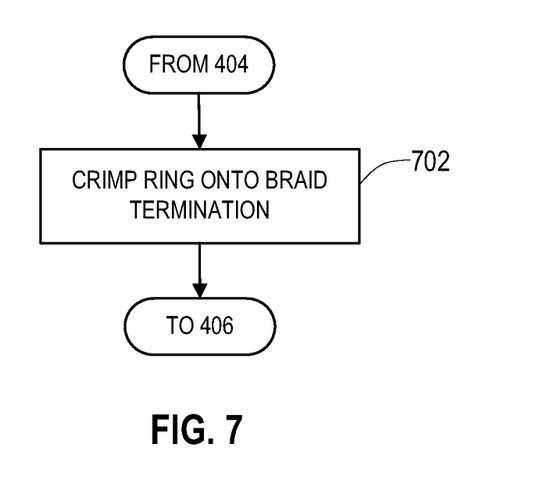
FIG. 7 shows another example of a logical flow of operations to add the shield layer with a crimped shield terminator to an existing lead or extension.

FIG. 7 shows an alteration to the operations 400 of FIG. 4 in order to provide the metal ring terminator. Immediately after operation 404 and prior to operation 406 of FIG. 4, the metal ring is placed over the end of the shield layer and is then crimped tightly against the shield layer at an operation 702. The outer insulative layer may then be positioned over the shield layer at the operation 406 as described above in relation to FIG. 4.

Figure 8:
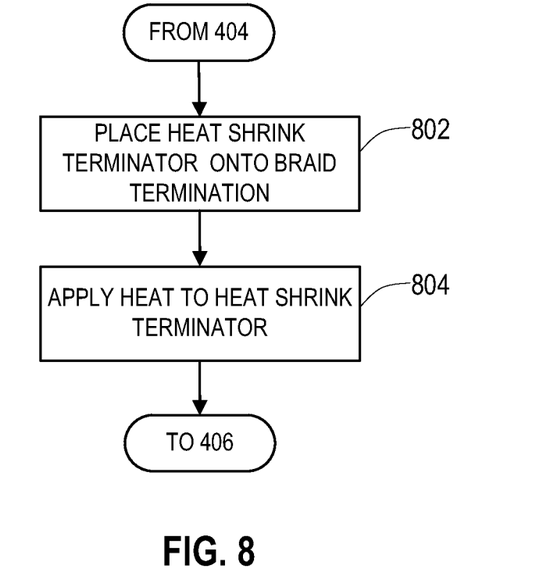
FIG. 8 shows another example of a logical flow of operations to add the shield layer with an additional insulative shield terminator to an existing lead or lead extension.

FIG. 8 shows an alteration to the operations 400 of FIG. 4 in order to provide the heat shrink terminator. Immediately after operation 404 and prior to operation 406 of FIG. 4, the heat shrink terminator is placed over the end of the shield layer at an operation 802. Heat is then applied to the heat shrink terminator at an operation 804 to cause the heat shrink terminator to tighten against the end of the shield layer. The outer insulative layer may then be positioned over the shield layer at the operation 406 as described above in relation to FIG. 4.

Figure 9:
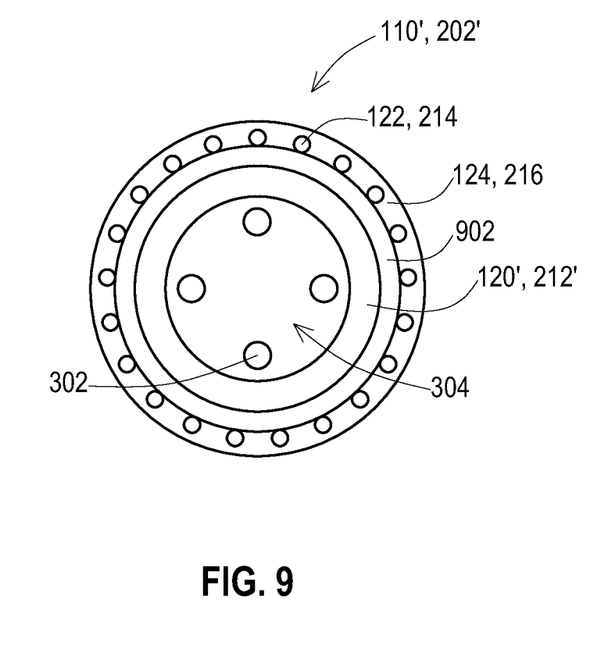
FIG. 9 shows a lateral cross-sectional view of a lead or lead extension having an added shield layer and an added inner insulative layer according to various embodiments.

FIG. 9 shows a cross-section of an alternative embodiment that adds an inner insulative layer onto the lead body of a lead 110' or lead extension 202' prior to adding the shield layer. This embodiment may be useful where the lead body of the existing lead 110' or lead extension 202' is a material that may not be appropriate for receiving the shield layer directly due to being too soft or lacking bonding strength to the metal of the shield layer and/or polymers of the outer insulative layer. For instance, the lead body 120', 212' may be a silicone material to provide a very high degree of flexibility. However, it may be appropriate to shield a portion of the lead body 120', 212' where the high degree of flexibility is not needed. For example, a lead being used for deep brain stimulation may need to be very flexible at the entry point to the brain where a sharp bend of the lead body is necessary. Yet it may be acceptable for that lead to be stiffer in the area where the lead passes by the ear. Therefore, in that section that may be stiffer, the inner insulative layer 902 may be added to the lead body 120', 212' where that inner insulative layer 902 may be a material such as a polyurethane heat shrink tubing.

The shield layer 122, 214 is applied onto the inner insulative layer 902 as in the prior embodiments. The inner insulative layer 902 protects the lead body 120', 212' which may be more vulnerable to damage from the shield layer 122, 214 due to being a very soft and flexible material. The outer insulative layer 124, 216 is then applied over the shield layer 122, 214 as discussed above for the prior embodiments.

Figure 10:
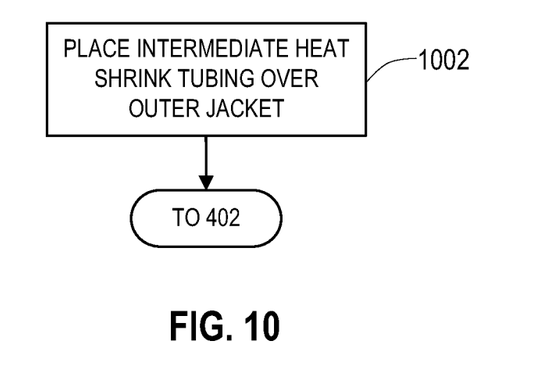
FIG. 10 shows another example of a logical flow of operations to add the shield layer and an inner insulative layer to an existing lead or extension.

FIG. 10 shows an alteration to the operations 400 of FIG. 4 in order to provide the inner insulative layer. Immediately before the operation 402 of FIG. 4, the heat shrink tubing which acts as the inner insulative layer 902 in this example is placed over the lead body 120', 212' at an operation 1002. Heat may be applied to the heat shrink tubing at this point or alternatively may be heated when heating the outer insulative layer. The lead 110' or lead extension 202' may then be positioned into the braiding machine at the operation 402 as described above in relation to FIG. 4 or may otherwise receive the shield layer 122, 214 and the operations of FIG. 4 proceed. The resulting lead or extension maintains flexibility where needed while being shielded in other areas.

While embodiments have been particularly shown and described, it will be understood by those skilled in the art that various other changes in the form and details may be made therein without departing from the spirit and scope of the invention.

What is claimed is:

1. A method of retrofitting an implantable medical component to improve MRI safety, comprising:
   loading the implantable medical component into a braiding machine;
   braiding wires onto an insulative lead body of the implantable medical component while using the implantable medical component as a mandrel; and
   applying an outer insulative layer onto the braided wires on the implantable medical component, wherein the implantable medical component is selected from the group consisting of a medical lead and a medical lead extension.

2. The method of claim 1, wherein the braided wires comprise tantalum.

3. The method of claim 1, wherein applying the outer insulative layer onto the braided wires comprises sliding a polymer heat shrink tubing onto the braided wires and heating the heat shrink tubing.

4. The method of claim 1, further comprising placing a terminator on an end of the braided wires.

5. The method of claim 1, wherein the insulative lead body defines a lumen.

6. The method of claim 5, wherein a conductor is present within the lumen.

7. The method of claim 6, wherein a proximal contact is coupled to a proximal area of the insulative lead body.

8. The method of claim 7, wherein the conductor is electrically coupled to the proximal contact.

* * * * *